(12) United States Patent
Brudnak

(10) Patent No.: US 6,783,757 B2
(45) Date of Patent: Aug. 31, 2004

(54) COMPOSITION AND METHOD FOR INCREASING EXORPHIN CATABOLISM TO TREAT AUTISM

(75) Inventor: Mark A. Brudnak, Port Washington, WI (US)

(73) Assignee: Kirkman Group, Inc., Lake Oswego, OR (US)

( * ) Notice: Subject to any disclaimer, the term of this patent is extended or adjusted under 35 U.S.C. 154(b) by 0 days.

(21) Appl. No.: 09/872,615

(22) Filed: Jun. 1, 2001

(65) Prior Publication Data

US 2002/0041871 A1 Apr. 11, 2002

Related U.S. Application Data

(60) Provisional application No. 60/208,800, filed on Jun. 1, 2000.

(51) Int. Cl.[7] .......................... A61K 38/54; A61K 38/48
(52) U.S. Cl. .............................. 424/94.65; 424/94.67; 424/94.66; 424/94.64; 424/94.63; 424/94.6; 514/23; 514/777
(58) Field of Search ........................... 424/94.65, 94.66, 424/94.67, 94.63, 94.64, 94.6; 514/23, 777

(56) References Cited

U.S. PATENT DOCUMENTS 5,885,618 A * 3/1999 Knap et al. .................. 424/499
6,251,391 B1 6/2001 Wilkinson et al.

FOREIGN PATENT DOCUMENTS

EP 0 372 702 * 6/1990
WO WO 97/39116 * 10/1997

OTHER PUBLICATIONS

Peptidose Enzyme Digistive Aid Project, Pangborn, J. 9/97.

* cited by examiner

Primary Examiner—Francisco Prats

(57) ABSTRACT

A composition for use in treating autism spectrum disorders. The composition preferably includes a genomeceutical type compound that increases the user's expression of DPPIV or like substances. The genomeceutical compound may include a sugar (such as a milk sugar), glucans, galactose and/or related material. The composition may also include one or more of a protease, peptidase or phytase. The inclusion of phospholipids, disaccharides, lipases and/or related substances in a composition for treating autism spectrum disorders and the function they provide is also disclosed.

5 Claims, No Drawings

COMPOSITION AND METHOD FOR INCREASING EXORPHIN CATABOLISM TO TREAT AUTISM

CROSS REFERENCE TO RELATED APPLICATIONS

This application claims the benefit of U.S. Provisional Application No. 60/208,800, filed Jun. 1, 2000, and having the same inventor as above and entitled Enzyme Formulation for Treating Autism.

FIELD OF THE INVENTION

The present invention relates to treating autism and, more specifically, to treating autism by increasing expression and/or activity of exorphin cleaving gene products. The present invention also includes the use of phytase and like substances and formulations containing enzymatic and phytase-like compounds for treating autism.

BACKGROUND OF THE INVENTION

Autism may be defined as a condition, usually present from childhood, that is characterized by self-absorption, a reduced ability to respond to or communicate with the outside world and behavioral dysfunction. An autistic individual may suffer from several maladies with the accumulated symptoms being categorized as autism spectrum disorders, referred to in the field as autism or ASD. Symptoms of autism include stimming, reduced eye contact, perseveration (repeating same activity for long periods), poor communication and social skills and heightened sound sensitivity, amongst others.

It has been estimated that from 1 in 2,000 to 1 in 300 persons suffer from autism with an initial manifestation of symptoms by age three. It is of interest to note that the overall percentage of persons exhibiting symptoms of autism is increasing, in some instances dramatically. As discussed below, this rise may be due in part to an increase in the percentage of persons receiving childhood vaccinations. Males are more likely to suffer from autism than females.

There are several theories related to the initial and continued cause(s) of autism. One theory relates to infection or inflammation in the stomach and/or intestines early in life and maladaptation of the immune system and other tissues to this inflammation.

Historically, the immune system has been thought to develop early in life through education of the cellular components within the thymus (T-cells) and spleen (B-cells). There, the various cells are trained to recognize self vs. non-self antigens and to take the appropriate action, or lack thereof, in response to any exposure. In the last decade, however, a new class of immune cells has been intensively studied. These cells never "see" the thymus or spleen and are educated solely in the intestinal tissues from which they arise. These intraepithelial lymphocytes (IEL), or "intestinal" epithelial lymphocytes, are an athymically derived T-cell subset expressing the $\gamma\delta$ TCR-CD3 complex along with CD8. The $\gamma\delta$ T cells in the epithelial tissues do not circulate as their $\alpha\beta$ T cell (thymically derived) relatives do.

Though the subject of much speculation, the IELs are thought to be a primordial immune system and the first to function in life. IELs have been shown to bind to mycobacterial antigens that are protease resistant and appear to have been selected to respond quickly to unique immune challenges. Since the mycobacterial antigens are protease resistant proteins, immune cells responsible for their removal would not benefit from an increased production of protease genes. The immune cells would tend to conserve energy and redirect efforts by, for example, turning off protease genes. Thus, various protease genes, including those that appear to be effective in breaking down pre-opioid compounds that are linked to autism (discussed below), may be down-regulated. In fact, DPPIV has been shown to be down regulated in autistics and is currently being used as a diagnostic marker for the disease. In addition, IELs may encourage apoptosis or quiescence of intestinal cells. This cell death or disablement may lead to the "leaky" intestinal wall condition often associated with autism and ASD. Down regulation of protease genes and formation of "leaky" intestines are examples of the apparently maladaptive response mentioned above.

It is believed that these or other conditions cause the digestive tract of a person with autism to function sub-optimally. Two important pioneers of this work, Reichelt and Shattock, observed a significant correlation between the symptoms of autism and an impaired ability to adequately digest peptides/proteins from dairy (casein) and wheat (gluten). During digestion, pre-opioid type compounds in the diet, typically from casein and gluten, are thought to be activated due to an incomplete breakdown of proteins. These exorphins (i.e., casomorphins and gluteomorphins or gliadinomorphin) are then easily transferred across the lumen of the gut into the circulation where they exert opioid-type action on the brain.

In theory, no enzyme digestion in the body is ever 100% complete. Statistically, some protein or peptide fragments will escape the digestive process and be absorbed. The larger fragments may be transferred across the lumen of the gut via the M-cells and active transport while the smaller fragments may simply diffuse. Coupling these phenomena with the characteristically "leaky" intestinal tract of an autistic, it becomes readily apparent how biologically significant quantities of peptides and, more specifically, exorphins can enter the circulation.

The exorphins are recalcitrant to endogenous proteolytic enzyme digestion due to the presence of a proline in the penultimate position of the peptide. The body relies on its own production of dipeptidyl-peptidase IV (DPPIV), in the gut and other cells, for the digestion of exorphins. DPPIV is a serine exo-peptidase that cleaves Xaa-Pro dipeptides from the N-terminus of oligo- and polypeptides. It was first reported as glycylproline naphthylamidase and has been named dipeptidyl aminopeptidase IV or postproline dipeptidyl peptidase IV in early work. As alluded to above, it is suspected that genes which produce DPPIV are down regulated in autistic individuals.

To compensate for the apparent lack of sufficient quantities of DPPlV and to generally rebuild proper functioning of an autistic individual's intestinal tract with regard to absorption and digestion, different approaches have been employed. Of these, enzyme therapy and probiotic supplementation have been favored and met a degree success. Enzyme therapy has typically been based on supplementation with large amounts of protease from different categories of proteolytic enzymes and these have included acid or carboxyl peptidases, peptidases with both endo- and exo-peptidase activity, and serine, cysteine and zinc protease. More recently exogenic DDPIV from animal (usually cow or pig) and plant source has been utilized. While enzyme therapy has had limited success, it is disadvantageous, amongst other reasons, in that many proteases, including DDPIV, are broken down in the stomach and do not reach the intestines in a functional state.

Probiotic supplementation has focused mainly on trying to rebuild the intestinal wall via a restoration of the naturally occurring bacterial flora. Common intestinal microflora are isolated from the human gut and cultured to form a "probiotic culture." Two approaches to the treatment of autistic dysbiosis using probiotic cultures have emerged. The first uses a wide variety of organisms and is something of a "shot-gun" approach. The second employs a more targeted approach by supplying very large numbers of viable organisms as high as 100 billion/gram. Both approaches have been based on clinically observed and published therapeutic benefits of probiotics and while they have met with limited success relative to no probiotic treatment, they do not adequately treat the syndromes associated with autism, suggesting that exorphin digestion is more than just an issue of microflora composition.

A need thus exists for a more effective manner of breaking down exorphins in the stomach and the intestinal tract of an autistic individual. A need also exists to increase expression of DPPIV and DPPIV like compounds from within an autistic individual's own body, i.e., overcoming the apparent down regulation of these or related genes. A need further exists for increasing the bioavailability of minerals that facilitate digestion reactions.

SUMMARY OF THE INVENTION

Accordingly, it is an object of the present invention to increase expression of DPPIV and/or related compounds in the gut of an individual with autism.

It is another object of the present invention to utilize ingestible materials that modify expression of DPPIV, QPP or another compound whose regulation is beneficial in treating autism.

It is another object of the present invention to provide various formulations that include material that affects the expression or activity of a gene product useful in treating autism and one or more proteases/peptidases for treating autism.

It is also an object of the present invention to provide various formulations for treating autism that include phytase (or phytase-like substances) and protease and/or material that affects the expression or activity of a gene product useful in treating autism.

It is a further object of the present invention to provide various formulations for treating autism that include phospholipids, disaccharidases and/or lipases.

These and related objects of the present invention are achieved by use of a genomeceutical composition and method for treating autism as described herein.

The attainment of the foregoing and related advantages and features of the invention should be more readily apparent to those skilled in the art, after review of the following more detailed description of the invention taken together with the drawings.

DETAILED DESCRIPTION

There are compounds or materials that when ingested can cause a gene to either alter its expression pattern (i.e., make more or less of its product), affect the fidelity of a gene (i.e., how well that gene product works) or affect the integrity of a gene (i.e., whether or not the gene is functional). These gene product affecting materials do not directly replace substances that are missing (e.g., an enzyme diminished by mutation), but actually alter the expression and/or functionality of the gene products.

Glucosamine is an example of such a material. Glucosamine has been shown to increase the level of transcription and translation of important genes. Adding glucosamine to a diet has been shown to increase both RNA and protein levels. The addition of glucosamine also increases the expression of leptin (a fat hormone), again suggesting an expression based response to the presence of glucosamine.

The present invention provides the novel approach of utilizing ingestible gene product affecting materials to treat autism. For example, in at least one embodiment discussed below, the present invention includes the use of the milk sugar galactose to modify (e.g., up regulate) DPPIV expression. This up regulation may occur in cells within the intestinal tract and possibly elsewhere. Although not concerned with autism, Smith et al have reported that galactose can increase the expression of DPPIV in cultured mouse intestinal wall cells (also known as enterocyte cells). (see Smith, M. W., James, P. S., Peacock, M. A., *Galactose Effects on Enterocyte Differentiation in the Mouse Jejunum.* Biochem Biophys Acta Jul. 10, 1991, 1093(2–3) :1446).

In furtherance of the present invention, studies (discussed below) were carried out based on the hypothesis that galactose might pass through the human stomach and increase expression of DPPIV in human intestinal wall cells and elsewhere. The increased amount of DPPIV would in turn achieve sufficient digestion of the pre-opioid exorphins to significantly reduce the symptoms of the autistic individual ingesting the galactose based composition.

In addition to galactose, the present invention may also include the use of other gene product affecting materials, various proteases and/or peptidases, compounds that increase up take of substances that facilitate gene expression, phospholipids, disacchradases, lipases, related compounds and combinations of these items. Various representative, but not exclusive, embodiments of the present invention are now discussed in more detail.

Formulation A

In one embodiment of the present invention, termed formulation A for purposes of the present discussion, galactose is provided as to increase expression of DPPIV. The galactose is preferably combined with other substances to enhance overall effectiveness. The other substances in the preferred embodiment of formulation A include: acid fast protease (AFP); bromelain and/or papain; peptidase concentrate; lactase and phytase.

If, in autistic individuals, the DPPIV gene has been silenced or attenuated (i.e., down-regulated), then the addition of galactose has the potential to reverse or circumvent the down-regulation. This positive regulation may occur not only in human intestinal wall cells (enterocytes), but in other cells where DPPIV or DPPIV-like enzymes are expressed (where a DPPIV-like enzyme is an enzyme that cleaves proline-containing peptide bonds in exorphina). It should also be recognized that DPPIV or like expression in cells other than human enterocyte cells may prove to be as or more beneficial than enterocyte cell expression. These other cells include, but not limited to, peripheral blood (immune) cells and other cells with suitable surface architectures and signaling cascades.

AFP is representative of a class of proteases that have high acid stability and function in the stomach to hydrolyze large proteins into smaller peptides. The presence of a large amount of this enzyme is important in promoting rapid hydrolyzation of large proteins. The preferred result is that exorphins are formed early (in the stomach) and are digested (also in the stomach) before they reach a point of absorption (in the intestines). Driving the reaction forward with large amounts of acid stable enzyme in the stomach allows more time for the body's endogenous enzymes, that have evolved to specifically digest exorphins, to work.

To further assist with this digestion a cysteine protease is preferably used. Bromelain and papain are examples of a cysteine protease. Bromelain is preferred over papain because research has suggested that bromelain has a wider specificity and function than papain. It has also been demonstrated that bromelain is an effective anti-inflammatory which may be significant in reducing the "leaky gut" characteristic of autistic individuals.

A peptidase concentrate component is preferably provided that exhibits endo- and exo-peptidase activity. It is further preferred that the peptidase concentrate mimics DPPIV activity and hence provides further exorphin digestion. A suitable peptidase concentrate, amongst others, is the Case-Glutenase concentrate available commercially from Kirkman Laboratories in Lake Oswego, Oreg.

Lactase is a disaccharidase that cleaves lactose into its component sugars fructose and galactose. The provision of lactase permits utilization of Formulation A (or others herein) by lactose intolerant people and increases that amount of available galactose. Cleaving lactose and sucrose and other disaccharides also reduces osmotic pressure in the intestines.

Phytase is preferably added for its ability to digest phytic acid which is present in plants such as corn, rice, wheat, soybean, and other beans, etc. Phytic acid can negatively affect absorption of minerals such as zinc, calcium, magnesium, copper, manganese, and iron. Phytase supplementation results in greater bioavailability of these minerals.

The components are generally available commercially and are preferably provided in a dry form, mixed and encapsulated, though other delivery methods may be utilized without departing from the present invention. The capsules are preferably taken with food. While the presence and concentration of the above ingredients may vary widely (as discussed to some extent herein below and as recognized by one skilled in the art given the teachings herein), in one embodiment formulation A may contain the following:

| | |
|---|---|
| 1. galactose | 100 mg; |
| 2. bromelain concentrate | 230 BTU; |
| 3. acid fast protease | 100 SAPU; |
| 4. peptidase concentrate | 10,000 AU; |
| 5. lactase | 300 LACU; and |
| 6. phytase | 125 PU. |

It should be recognized that these values are intended to be representative and in no way limit the present invention.

This formulation A was given to 22 autism sufferers over a twelve-week period. Thirteen behavioral parameters were monitored including eye contact, socialization, attention, mood, hyperactivity, anxiety/compulsion, stimming, comprehension, speech, sound sensitivity, digestion, sleep and perseveration. Observers scored the patients every two-weeks for the twelve-week period. A Student's T-test was used for statistical significance determination.

Overwhelming positive trends were seen for each parameter with the greatest improvements in socialization is and hyperactivity (90% and 80%, respectively) and the lowest improvements in stimming, speech and sound sensitivity, each scoring around 50% improvement.

The functioning of galactose is believed to be at at least two levels. A first level is increasing the gut expression of the DPPIV gene. This increased expression allows for a greater level of the DPPIV enzyme in human enterocytes and other cells which in turn achieves a more thorough breakdown of any exorphins.

A second level is that galactose serves as a fuel source of the beneficial microflora (i.e., probiotics) in the gut. This is important because the probiotic organisms themselves contain enzymes capable of breaking-down the subject exorphins. Varmanen et al recently showed that probiotic organisms, currently utilized as health supplements, contain an analogue of the DPPIV enzyme (e.g., PepX) which is known to be able to digest exorphins. With over $10^{11}$ microorganisms in the gut, the contribution of probiotic enzymatic activity may exceed that of the enterocytes. It is well documented that galactose is a prebiotic (i.e., stimulates growth of probiotics) and can increase the number of probiotics in the gut.

It is theorized thus that the level of self-produced DPPIV enzyme in the intestinal tract and the level of DPPIV-type activity (contributed by bacterial flora) are increased. It is further theorized that the ability of the AFP to cause early exorphin formation (in the stomach) and the increased levels of DPPIV production result in sufficient exorphin digestion in the gut that the levels of exorphin absorption drop below a threshold required for manifestation of the noted autistic symptoms.

Variations of Formulation A

It should be recognized that while Formulation A preferably has at least the listed six ingredients, the present invention may include combinations of less than all of the listed ingredients, as determined by the limits of prior art. For example, the combination of an ingestible gene product affecting material for treating autism and proteases/peptidase is within the present invention as is the combination of such an ingestible gene product affecting material and phytase or a phytase like compound. If a patient does not have milk in their diet or is not lactose intolerant then lactase may not be necessary. Further variations are suggested elsewhere herein and others yet would be apparent to skilled practitioners given the teachings herein. Given the exponential combination of ingredients all variations are not specifically called out, though it should be recognized that they are intended to fall within the present invention.

Beta Glucans and QPP

Recently, a new peptidase (quiescent cell proline dipeptidase or QPP) from peripheral blood mononuclear cells (PBMCs) has been cloned and investigated. QPP is structurally and functionally related to DPPIV, but is more often found in the peripheral blood cells. Interestingly, QPP shares little sequence homology with DPPIV. These enzymes (DPPIV, QPP and others) are among the few enzymes that have the ability to cleave proline-containing peptide bonds. The exorphin opioid type peptides containing proline are generally resistant to degradation as smaller peptides.

Notwithstanding increased levels of DPPIV produced by the enterocytes by the addition of galactose, there may still be opioid peptides that reach circulation. If the QPP gene can be up-regulated, then exorphins that do manage to survive across the lumen of the gut are more likely to be digested once inside the circulatory system.

At the present time, there is preliminary data that suggests that stimulation of the TCR causes an up-regulation of the QPP gene. The TCR can be stimulated by a number of known factors. These include, but are not limited to, antibodies, lectins, and macrophages. While certain natural and potentially safe lectins may exist and be shown useful in the future, current technology and regulatory issues makes mammalian lectins impractical. Also, as shown by empirical data, plant lectins can be extremely dangerous. Antibodies offer some potential, but there are also many problems associated with their use. These range from their ethical production to safety. Encouragement of macrophage participation in accordance with the present invention solves most of these problems and presents an opportunity for therapeutic application of genomeceuticals.

It is well known that in the gut, cellular components of bacteria, fungi, and molds can stimulate gut-associated macrophages. These macrophages constantly sample and survey the gastrointestinal tract for foreign antigens. The cellular components responsible for the stimulation of macrophages have been well documented and include not just proteins, but carbohydrates such as the beta glucans present in cell walls of microorganisms.

When macrophages are exposed to beta glucans, such as the yeast cell wall beta-1,3/1,6-glucan, they become non-specifically stimulated so that subsequent antigen exposure results in a much more robust immune response than would otherwise happen. Among those responses is the secretion of cytokines and the processing and subsequent presentation of antigens to T-cells. The role of antigen presentation is accomplished through interaction with the TCR. The bound TCR then transduces a signal to the nucleus directing an altered expression pattern which includes modified expression of available QPP. QPP is then secreted into circulation and is free to digest any exorphins present. Glucans have also been shown to up-regulate transcription factors in the cell nucleus. Hence, glucans can serve as ingestible material for increasing expression of QPP.

Accordingly, in another embodiment, the present invention includes one or more of the components of Formulation A with glucans and/or QPP (or their analogues).

Other Materials/Sugars

Lactose, fructose, sucrose, glucose, etc., are sugars that may be present in milk, as is galactose. The presence of one or more of these sugars may cause the intestinal cells to produce enzymes, including DPPIV like enzymes, that are effective in breaking down milk proteins and milk protein by-products (such as exorphins, amongst others). Thus, while galactose is a preferred sugar, it is possible that one or more of these other sugars and/or related compounds may exhibit efficiency in promoting expression of DPPIV like enzymes. Furthermore, the provision of lactose and lactase would provide galactose as a by-product.

Thus, including one of these sugars or a related compound as a substitute for or in addition to the galactose of Formulation A or with any variation of the components or Formulation A or their analogues or any other variation alluded to herein is within the present invention.

Protease/Peptidase

While Formulation A includes a particular protease and peptidase arrangement, it should be recognized that other protease and peptidase arrangements may be utilized without departing from the present invention. These include carboxyl, serine, and zinc proteases and any other proteases that would be efficacious and suitable. Other peptidase concentrates or specific peptidase compounds may be utilized.

These other proteases and peptidase may be used as substitutes for or in addition to the component(s) of Formulation A or other components mentioned herein.

Phytase

In addition to Formulation A, the present invention includes both (1) the combination of phytase and an ingestible material that affects endogenously produced gene products for treating autism and (2) the combination of phytase and a protease and/or peptidase for treating autism.

Various phytase like compounds are suitable for use in the present invention, where phytase like refers to compounds that increase the bioavailability of one or more of the listed minerals.

Phospholipids

Phospholipids may be provided in combination with less, all or more of the ingredients of Formulation A or other variations alluded to herein. Phospholipids would serve to rebuild cell walls and help heal the leaky guts of autistic individuals. A representative dose of phospholipids could be 300 mg of phosphotidyl serine or the like.

Disaccharidase

Lactase, sucrase and/or other disaccharidases may be provided in accordance with the present invention. The functions of these compounds is discussed in part above with the discussion of lactase. The disaccharidase(s) may be provided as a substitute for or in addition to other components and other varied formulations discussed or alluded to herein.

Lipase and Other Enzymes

Lipase, amylase and other related enzymes may also be provided in accordance with the present invention. Amylase liberates glucose from carbohydrates, and the, liberated carbohydrate may serve as a material that positively affects an endogenously produced gene product as discussed above. A fungal based amylase is available commercially. Other amylases may also be suitable.

Lipase serves to digest fat. Undigested fats lead to loose stools which are a condition associated with autism. Animal pancreatic lipase or a similar lipase that mimics human pancreatic lipase is preferred, though other lipase may be suitable. Lipases are available commercially.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A composition comprising: galactose, an acid fast protease, a peptidase, a cysteine protease and phytase.

2. The composition of claim 1, wherein the cysteine protease is selected from the group consisting of: bromelain and papain.

3. The composition of claim 1, wherein the acid fast protease is selected from the group consisting of: carboxyl protease; serine protease; zinc protease.

4. The composition of claim 1, further comprising lactase.

5. The composition of claim 1, further comprising quiescent cell proline dipeptidase.

* * * * *